United States Patent [19]

Hansche

[11] Patent Number: Plant 6,976

[45] Date of Patent: Aug. 8, 1989

[54] VALLEY GEM

[75] Inventor: Paul E. Hansche, Davis, Calif.

[73] Assignee: The Regents of The University of California, Berkeley, Calif.

[21] Appl. No.: 107,121

[22] Filed: Oct. 9, 1987

[51] Int. Cl.[4] ..... A01H 5/00

[52] U.S. Cl. ..... Plt./43

[58] Field of Search ..... Plt./43

*Primary Examiner*—Robert E. Bagwill

*Attorney, Agent, or Firm*—Townsend and Townsend

[57] ABSTRACT

A new and distinct dwarf peach variety suitable for commercial and/or home garden use. This variety has a unique origin and differs from selections 'Valley Sun' and 'Valley Red' in that the fruit ripens much later than either of the other said selections.

1 Drawing Sheet

DESCRIPTION

This invention relates to a new and distinct variety of dwarf peach tree which resulted from a complex cross, the pedigree named 'Valley Gem' of which is set forth below:

$$\text{4,27-116-22,102-66} \xleftarrow[\text{54P454 Anderson}]{\text{CalRed}} \text{x}$$

The last step of self pollination of 22,102-66 was made in 1980.

The invention of genotype 'Valley Gem' (4,27-116) was discovered in 1983 and subsequently asexually propagated at the University of California, Davis, Calif. in 1986. Thereafter it was placed in a selection block at the University of California at Davis, and at the Kearney Horticultural Field Station, Fresno County, Calif. and evaluated. The evaluation revealed the merit of this new dwarf peach tree and resulted in its selection as a promising cultivar.

Figure 1:
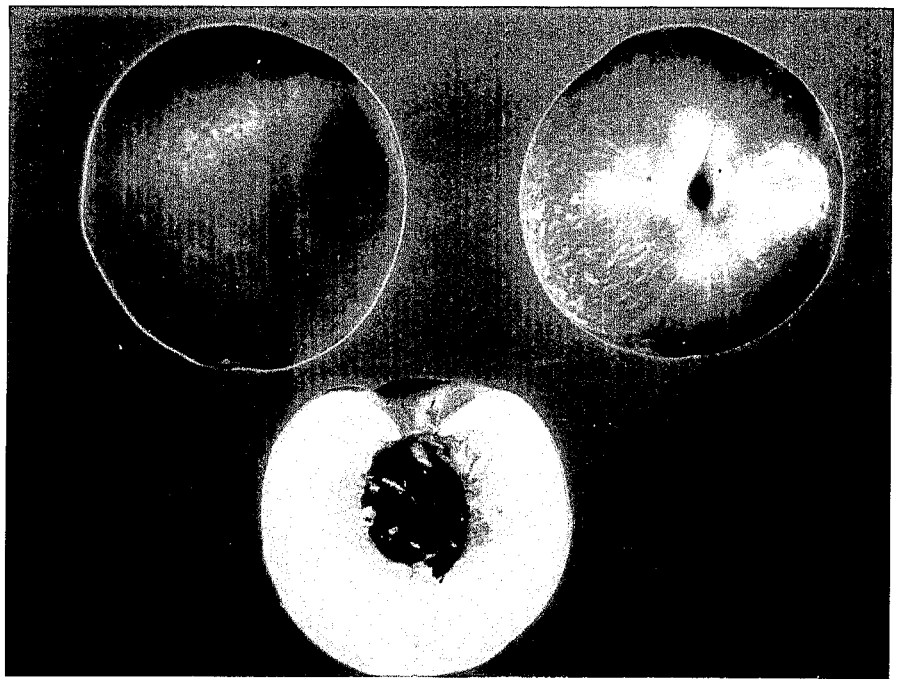
FIG. 1 illustrates peaches of the new cultivar which are typical in size, shape and color.
Figure 2:
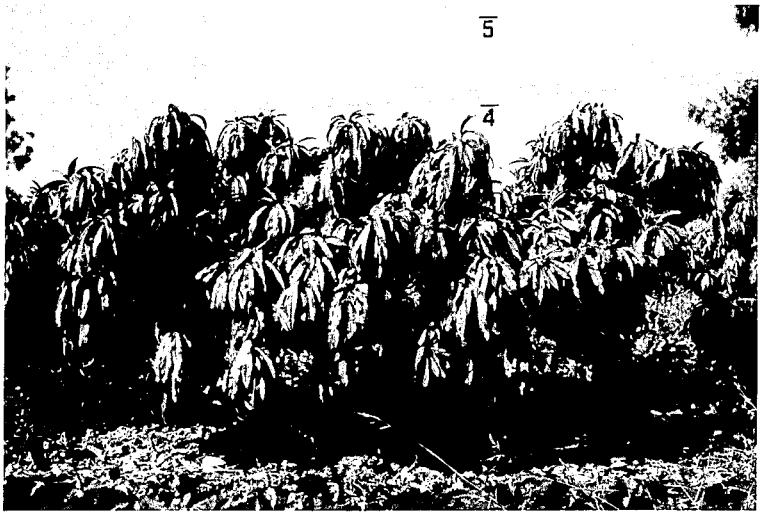
FIG. 2 illustrates a tree of the new cultivar which is typical in size, shape and color.

The characteristics that most distinguish this new dwarf tree from other dwarf peach cultivars is the excellent red blush that splashes over about 80% of the fruit surface by the time the fruit reaches shipping maturity, its smooth flesh and its firmness.

The fruit of this genotype is of very good eating quality; being sweet, but with an excellent flavor and a moderate aroma. The flesh is a clear amber-yellow color, without any red until nearly fully ripe.

The characteristics of this new dwarf peach tree, described below in detail, were observed upon its discovery and subsequently through the evaluation period. The color terminology as used herein is in accordance with Nickerson Color Fan, published and distributed by Munsell Color Co., 10 East Franklin Street, Baltimore, Md.

Tree:

*Genotype.*—Homozygous dw/dw.

*Size.*—About 5 ft in August of its 6th year at Davis (5–7 ft at maturity) vigorous; spherical. Current seasons shoots — Stout with a leaf internode distance of 7.0±3 mm; strong yellow green (2.5GY7/10), tinged red where exposed.

*Trunk.*—Little if any trunk.

*Branches.*—Stout brown to reddish brown (moderate olive 10Y4/3 to brownish grey 2.54); bark rough; peeling off in recurved platelets which adhere tightly; on younger branches growth cracks longitudinally striated showing light brown beneath (moderate olive brown 2.54).

*Lenticels.*—Moderately numerous, medium size, relatively inconspicuous with low, raised lips.

Leaves: From the middle of shoots 20 to 24 cms long.

*Size.*—Medium; 17±1.5 cm long×3.0±0.5 cm wide.

*Shape.*—Elliptic-lanceolate; base acuminate; apex long, acute-acuminate. Flat to somewhat recurved; apex more or less twisted.

*Blade.*—Thin; dark green above (dark yellowish green 10GY4/5), lighter below. Margin crenate. Midrib sparsely puberulent laterally, next to blade.

*Petiole.*—Short, 1.1±0.18 cm long; moderately thick; channeled on ventral surface; strong yellow green 7.5GY6/8.

*Glands.*—Reniform, usually 8 or more on upper half of the petiole and on the base of the blade.

Flowers: 1–2 per node.

*Corolla.*—Color and surface red to greenish depending upon exposure; glabrous.

*Calyx lobes.*—Separate; almost conic in shape, apex generally pointed. 4 mm at base by 4 mm long. Lobes reflexed about 90.

*Petals.*—Showey; broad ovate to nearly round; 13 mm wide×18 mm long to 18 mm wide×18 mm long; clear pink. Margin more often slightly eroded and/or nicked or slightly cleft at apex, flattish. Claw 1–2 mm medium long; medium stoutness.

Fruit:

*Ripe.*—August 20th.

*Crop.*—Moderate for tree.

*Size.*—Medium large; average weight of fruit 230±23 gms.

*Pubescence.*—Short, light.

*Shape.*—Slightly oblong. Length 82±8 mm×cheek diameter 78±7 mm×suture diameter 78±7 mm. Fairly regular, one half often slightly larger, or symmetrical with a somewhat protruding suture lip; apex depressed, or with a short, fleshy tip. Base may slope slightly toward the ventral suture. Ventral aspect: Broad elliptic to broad ovate; truncate at base, rounded or truncate at apex; halfs nearly equal to 1 noticeably large. Axial aspect: Nearly round; the ventral side somewhat thinner than the ventral side.

*Base.*—Somewhat variable; broad oval in outline. Medium shallow depth, conical; rather small; flattened at right angles to the fruit axis.

*Suture.*—The suture edge is smooth, or more commonly somewhat protruding; one-half often somewhat larger and forming a lip.

*Apex.*—The stylar scar a small dot, sometimes raised on a low fleshy tip. Rather deeply creased apically, the crease running somewhat past the stylar scar, to rounded and not at all depressed with the apical point occasionally a low, fleshy tip.

*Pit cavity.*—Not noticeable.

*Color.*—Ground color of firm ripe fruit is a rich brilliant yellow 5Y9/9 to a moderate orange yellow 10YR8/10 for soft ripe fruit. Blush: 80–10% of the fruit is covered with a strong reddish orange blush 7.5R5/13. About 10% of the blush is a deeply yellowish pink 5R6/11.

*Flesh color.*—A color between 5Y9/9 brilliant yellow and 2.5 YR9/3 light yellow pink. Clear, bright, attractive. No red except for occasional short radiating lines of red near cavity.

*Cavity color.*—Moderate brown 5R3/3 to dark reddish orange 7.5R4.

*Adhesion.*—Freestone.

*Flesh.*—Medium thick, firm-melting; moderately fine.

*Flavor.*—Eating quality very good. Sweet with a mild sub acid flavor.

*Stone.*—Medium size; somewhat long elliptic to slightly obovate; moderately plump. The grooves of medium depth and width rounded. Color dark red brown (moderate brown 5.4R3/3).

*Seed.*—Ovate; moderately plump; testas brown (strong brown 5.4 4/5).

I claim:

1. The new and distinct variety of peach tree herein described and illustrated and identified by the characteristics enumerated above.

* * * * *